United States Patent
Carmi

(10) Patent No.: US 7,480,362 B2
(45) Date of Patent: Jan. 20, 2009

(54) METHOD AND APPARATUS FOR SPECTRAL COMPUTED TOMOGRAPHY

(75) Inventor: Raz Carmi, Haifa (IL)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 12/091,751

(22) PCT Filed: Oct. 3, 2006

(86) PCT No.: PCT/IB2006/053618

§ 371 (c)(1),
(2), (4) Date: Apr. 28, 2008

(87) PCT Pub. No.: WO2007/049168

PCT Pub. Date: May 3, 2007

(65) Prior Publication Data

US 2008/0260094 A1 Oct. 23, 2008

Related U.S. Application Data

(60) Provisional application No. 60/596,894, filed on Oct. 28, 2005.

(51) Int. Cl.
*A61B 6/00* (2006.01)

(52) U.S. Cl. .............. 378/19; 378/5; 378/98.9

(58) Field of Classification Search ............... 378/4–20, 378/91, 98.8, 98.9, 901; 250/370.08, 370.09
See application file for complete search history.

(56) References Cited

U.S. PATENT DOCUMENTS

| | | | |
|---|---|---|---|
| 4,309,606 A | 1/1982 | Bjorkman et al. | |
| 4,476,384 A | 10/1984 | Westphal | |
| 4,835,703 A * | 5/1989 | Arnold et al. | ............... 702/193 |
| 5,349,193 A | 9/1994 | Mott et al. | |
| 6,470,285 B1 | 10/2002 | Atwell | |
| 6,901,337 B2 | 5/2005 | Tanaka et al. | |

FOREIGN PATENT DOCUMENTS

WO 0133252 A1 5/2001

* cited by examiner

*Primary Examiner*—Courtney Thomas

(57) ABSTRACT

An apparatus receives signals generated by a detector (100) sensitive to ionizing radiation such as x-rays. A differentiator (204) generates an output indicative of the rate of change of the detector signal. A discriminator (206) classifies the amplitude of the differentiator (204) output. An integrator (208) triggered by the output of the discriminator (206) generates outputs indicative of the detected photons. One or more correctors (24a, 24b) corrects for pulse-pileups, and a combiner (25) uses the outputs of the correctors (24a, 24b) to generate an output signal indicative of the number and energy distribution of the detected photons.

20 Claims, 6 Drawing Sheets

METHOD AND APPARATUS FOR SPECTRAL COMPUTED TOMOGRAPHY

CROSS REFERENCE TO RELATED APPLICATIONS

This application claims the benefit of U.S. provisional application Ser. No. 60/596,894 filed Oct. 28, 2005, which is incorporated herein by reference.

The present invention relates to the field of spectral computed tomography (CT). It also relates to the detection of x- and other radiation where it is desirable to obtain information regarding the energy or energy spectra of the detected radiation. It finds particular application in medical imaging, and also has application in non-destructive testing and analysis, security applications, and other applications where energy discrimination capabilities are useful.

CT scanners provide useful information about the structure of an object under examination. Thus, for example, CT scanners have gained wide acceptance in the field of medical imaging, where they are routinely used to provide valuable information regarding the physiology of patients. While they have proven to be extremely useful in clinical practice, the utility of CT scanners could be enhanced by providing additional information about the material composition of the object being examined, especially where the different materials have similar radiation attenuations.

One way to obtain material composition information is to measure the x-ray attenuation of the object at different x-ray energies or energy ranges. This information can be utilized to provide valuable information regarding the material composition of the object under examination.

Photon counting detectors have been used in nuclear medicine applications such as single photon emission computed tomography (SPECT) and positron emission tomography (PET). Such detectors have included scintillator-based detectors such as those based on lutetium orthosilicate ($Lu_2SiO_5$ or LSO), bismuth germanate (BGO) and sodium iodide (NaI) together with a photodetectors such as photomultiplier tubes (PMTs). Still other scintillator materials such as $Gd_2SiO_5$ (GSO), $LuAlO_3$ (LuAP) and $YAlO_3$ (YAP) are also known. In addition, direct conversion detectors such as cadmium zinc telluride (CZT) have been used. As a rule, photon counting detectors have a relatively greater sensitivity than traditional CT detectors. Moreover, photon counting detectors generally provide information about the energy distribution of the detected radiation, which has been used in SPECT and PET application for useful purposes such as correcting for the effects of scatter.

More particularly, such detectors typically produce an output pulse in response to an ionizing radiation photon. A typical pulse includes a fast rising signal portion followed by a slower decay portion. The relatively longer decay, which is dominated by the scintillator or direct conversion material, is the main limitation in fast photon counting, even when a high speed signal processing apparatus is used. As the photon count rate increases, the probability that two or more events will overlap, either partially or completely is increased. This phenomenon is known as pulse pile-up.

While photon counting detectors have proven useful in SPECT and PET, CT applications require a relatively higher count rate and wider dynamic range. At these relatively higher count rates, pulse pile-up becomes an even more significant issue. Accordingly, it would be desirable to provide for a more effective utilization of the information provided by photon counting detectors in spectral CT and other applications where relatively higher count rates are encountered.

Aspects of the present invention address these matters, and others.

According to a first aspect of the present invention, an apparatus includes a radiation sensitive detector which produces an output in response to ionizing radiation, a discriminator which produces first and second outputs based on the rate of change of the detector output, a first integrator triggered by the first discriminator output which generates a first integrator output, a second integrator triggered by the second discriminator output which generates a second integrator output, and a first corrector which uses the first and second integrator outputs to generate a first output indicative of detected radiation having a first energy range and a second output indicative of detected radiation having a second energy range. The first corrector corrects for pulse pile-ups in the detector output.

According to another aspect of the invention, a method includes the steps of measuring a rate of change of an output signal produced by a radiation sensitive detector in response to an ionizing radiation photon, updating a first value if the rate of change is in a first range, updating a second value if the rate of change is in a second range, repeating the steps of measuring, updating the first value, and updating the second value for a plurality of photons, generating a first output indicative of photons detected in a first energy range, and generating a second output indicative of photons detected in a second energy range. The first and second outputs are a function of the first and second values.

According to another aspect of the present invention, a method includes estimating the energy of an ionizing radiation photon detected by a radiation sensitive detector, updating one of at least first and second values depending on the estimated energy, repeating the steps of estimating and updating for photons detected during a pre-selected time period, using the first and second values to generate a first output indicative of detected photons having a first range of energies and a second output indicative of detected photons having a second range of energies. The first and second outputs include corrections for detector pulse pile-ups.

Those skilled in the art will appreciate still other aspects of the present invention upon reading an understanding the attached figures and description.

The present invention is illustrated by way of example and not limitation in the figures of the accompanying drawings, in which like references indicate similar elements and in which.

Figure 4A:
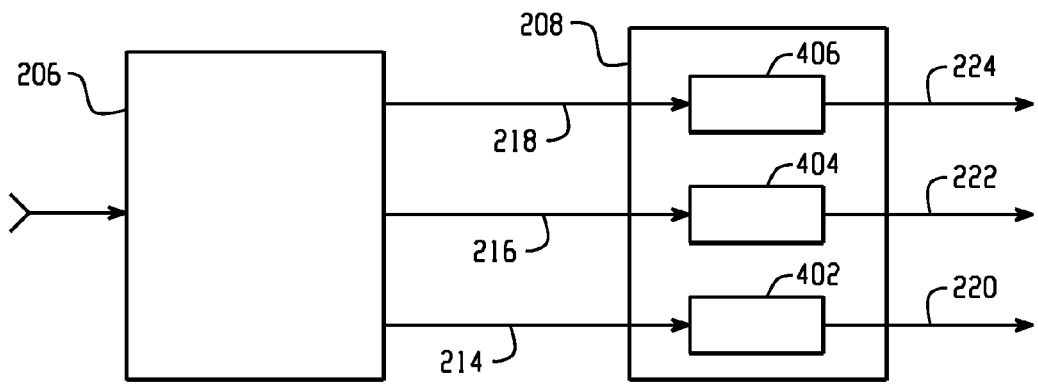
Figure 4B:
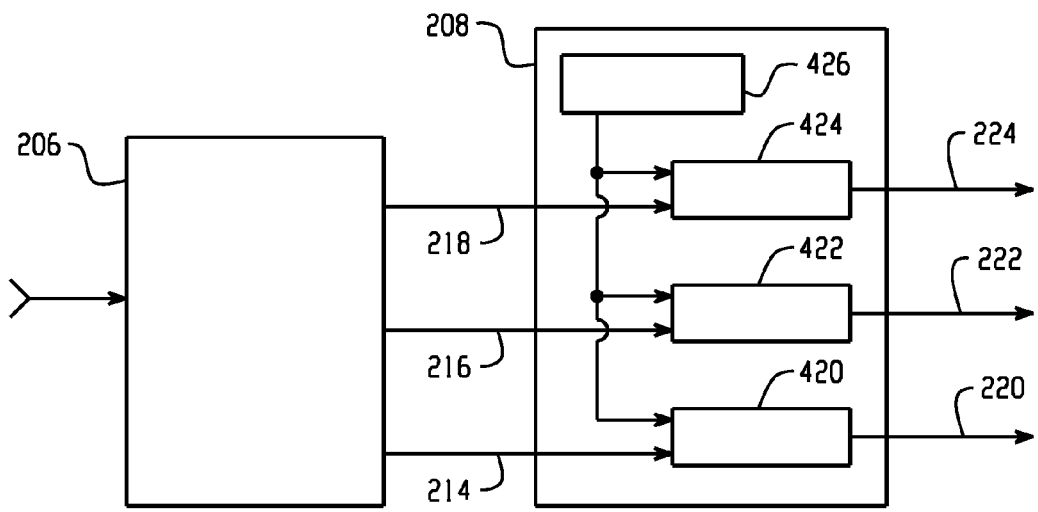
Figure 4C:
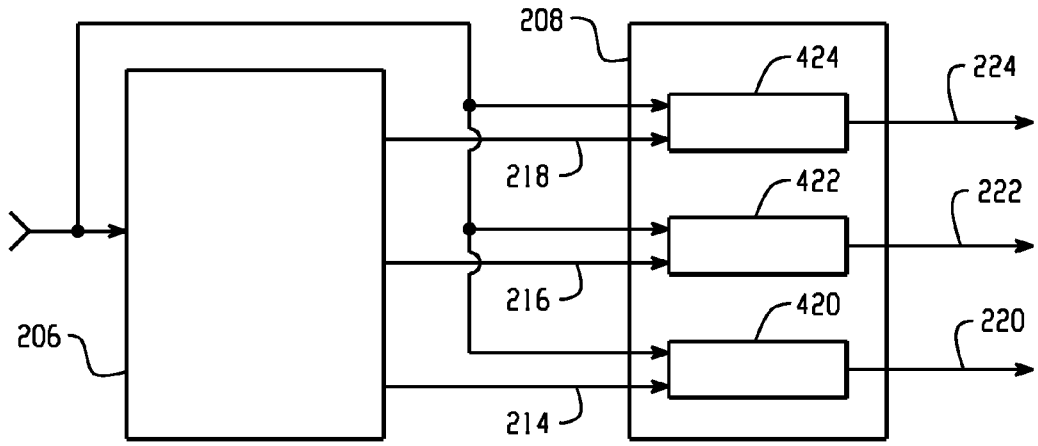

FIGS. 4a, 4b, and 4c depict respective implantations of an integrator.

Figure 5:
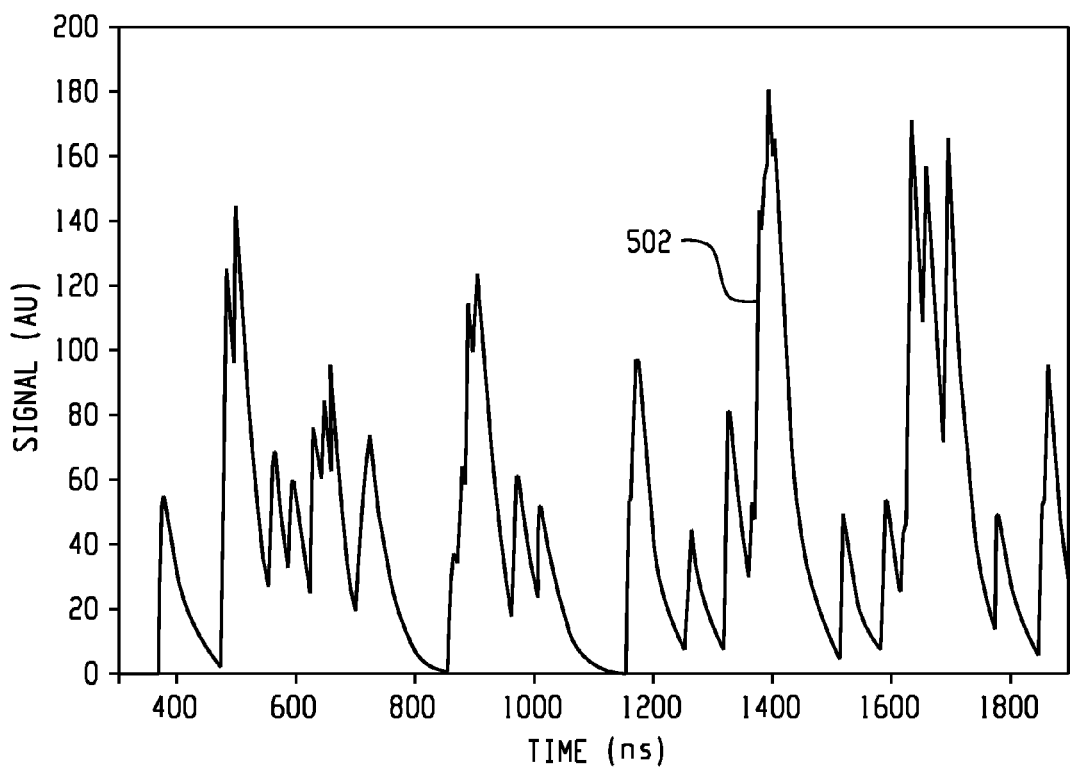

FIG. 5 depicts a simulated signal resulting from detection of radiation by a detector element.

Figure 6:
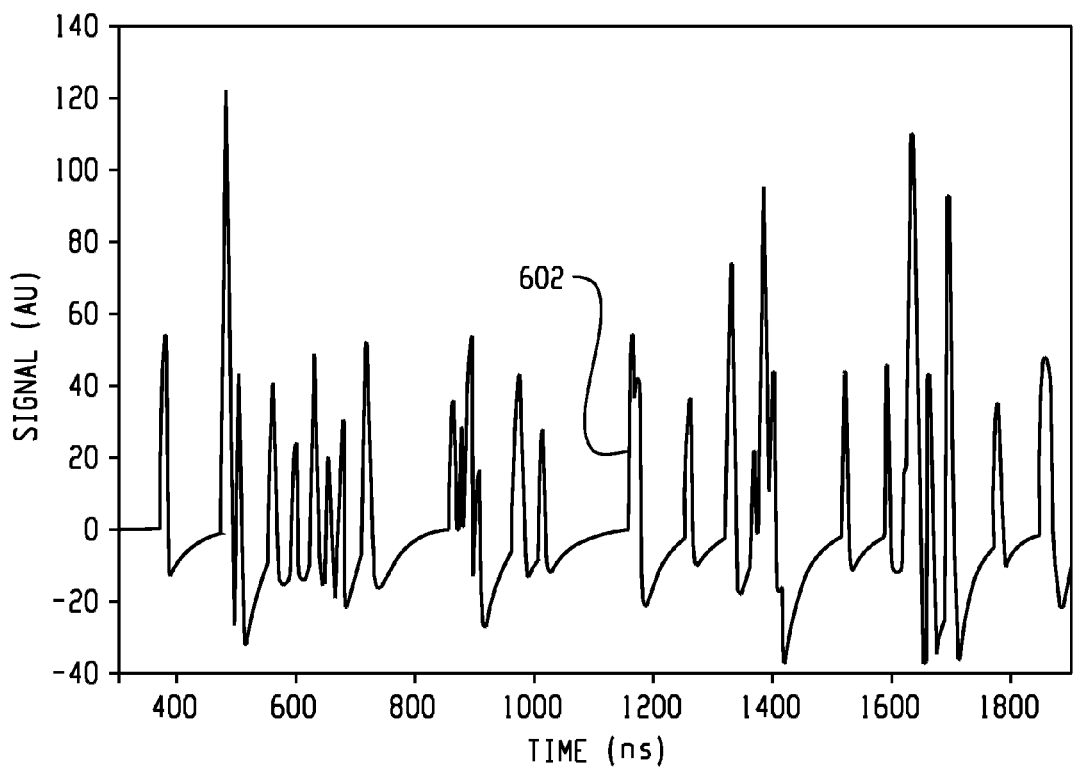

FIG. 6 depicts a simulated differentiator output.

Figure 7:
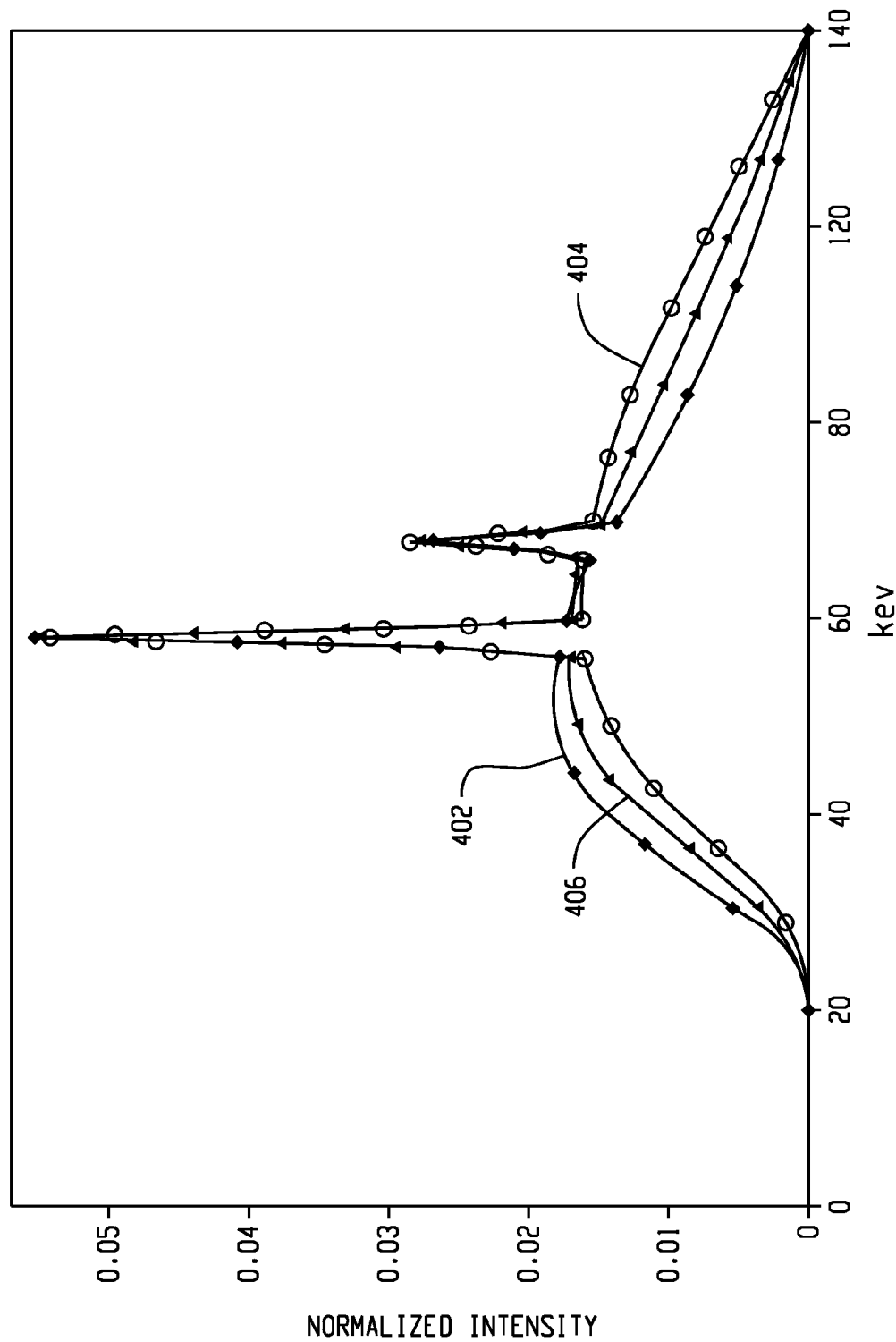

FIG. 7 depicts energy spectra used in a simulation.

Figure 8:
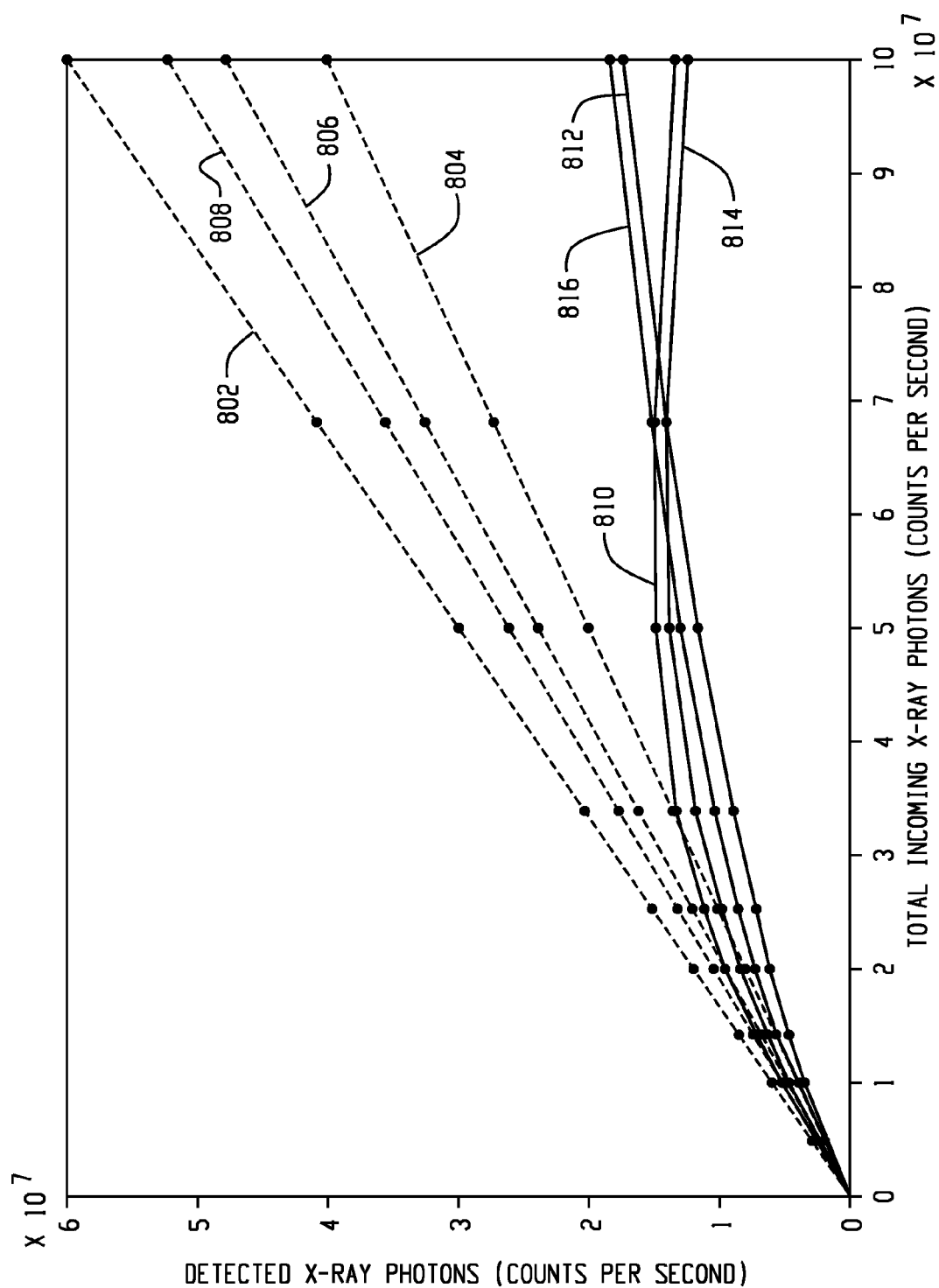

FIG. 8 depicts actual and measured photon count rates resulting from a simulation.

Figure 1:
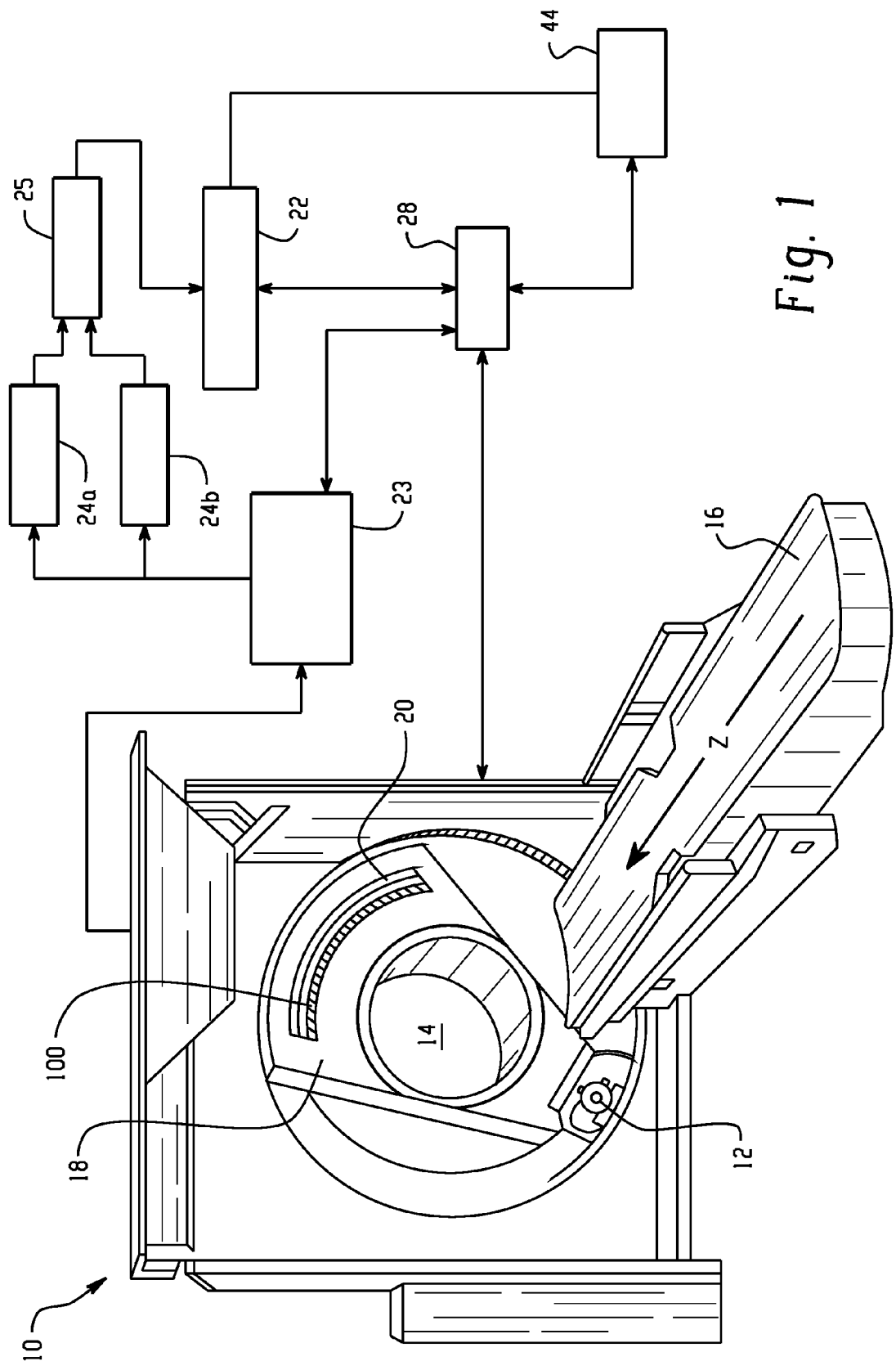
FIG. 1 depicts a CT scanner.

With reference to FIG. 1, a CT scanner includes a rotating gantry 18 which rotates about an examination region 14. The gantry 18 supports an x-ray source 12 such as an x-ray tube. The gantry 18 also supports an x-ray sensitive detector 20 which subtends an arc on the opposite side of the examination region 14. X-rays produced by the x-ray source 12 traverse the examination region 14 and are detected by the detector 20. Accordingly, the scanner 10 generates scan data indicative of the radiation attenuation along a plurality of projections or rays through an object disposed in the examination region 14.

A support 16 such as a couch supports a patient or other object in the examination region 14. The support 16 is preferably movable in the longitudinal or z-direction. In a helical scan, movement of the support 16 and the gantry 18 are coordinated so that the x-ray source 12 and the detectors 20 traverse a generally helical path relative to the patient.

The detector 20 includes a plurality of detector elements 100 disposed in an arcuate array extending in the transverse and longitudinal directions. In the case of a single slice detector, the detector elements 100 are arranged in an arcuate array extending in the transverse direction. For CT applications, the detectors elements 100 are preferably photon counting detectors based on relatively fast scintillators such as $Lu_2SiO_5$ (LSO), $Gd_2SiO_5$ (GSO), $LuAlO_3$ (LuAP) or $YAlO_3$ (YAP), in conjunction with a photodetector such as a photomultiplier or a photodiode. These scintillators have decay time constant of approximately 40 ns, 40 ns, 18 ns, and 24 ns respectively, and a rise time constant of the order of 1 ns. The detector elements 100 can be also based on direct conversion material such as CdZnTe (CZT). Other scintillator materials, direct conversion materials, or photon counting detector technologies may also be implemented. Each detector element 100 obtains a plurality of readings as the detector 20 rotates about the examination region. The time period over which a reading is obtained is a function of a number of design considerations, such as the sensitivity of the detectors, the desired transverse resolution, the gantry rotation speed, and the like. A suitable reading period can be on the order of 0.2 to 0.3 milliseconds, although other reading periods can be implemented.

Depending on the configuration of the scanner 10 and the detector 20, the x-ray source 12 generates a generally fan, wedge, or cone shaped radiation beam which is approximately coextensive with the coverage of the detector 20. Moreover, a so-called fourth generation scanner configuration, in which the detector 20 spans an arc of 360 degrees and remains stationary while the x-ray source 12 rotates, may also be implemented, as may detectors arranged in flat panel array. Moreover, in the case of a multi-dimensional array, the various detector elements 100 may be focused at the x-ray source 12 focal spot and hence form a section of a sphere.

A data acquisition system 23 preferably located on or near the rotating gantry 18 receives signals originating from the various detector elements 100 and provides necessary analog to digital conversion, multiplexing, interface, data communication, and similar functionality. As will be described below, the data acquisition system provides outputs indicative of the number and energy distribution of the x-ray photons detected by each of the detector elements 100 at each of a number of reading periods.

As will also be described below, first 24a and second 24b correctors and a combiner 25 correct for deviations in the count and energy distribution information produced by the data acquisition system. In one implementation, the correctors 24 and combiner 25 are implemented via computer readable instructions stored on a disk, memory, or other storage media which are executed by one or more of the computer processors associated with the reconstructor 26 following acquisition of the scan data.

The reconstructor 22 reconstructs the data from the corrector to generate volumetric data indicative of the interior anatomy of the patient. In addition, the data from the various energy ranges is processed (before reconstruction, after reconstruction, or both) to provide information about the material composition of the object under examination.

A controller 28 coordinates the various scan parameters as necessary to carry out a desired scan protocol, including x-ray source 12 parameters, movement of the patient couch 16, and operation of the data acquisition system 23.

A general purpose computer serves an operator console 44. The console 44 includes a human-readable output device such as a monitor or display and an input device such as a keyboard and mouse. Software resident on the console allows the operator to control the operation of the scanner by establishing desired scan protocols, initiating and terminating scans, viewing and otherwise manipulating the volumetric image data, and otherwise interacting with the scanner.

Figure 2:
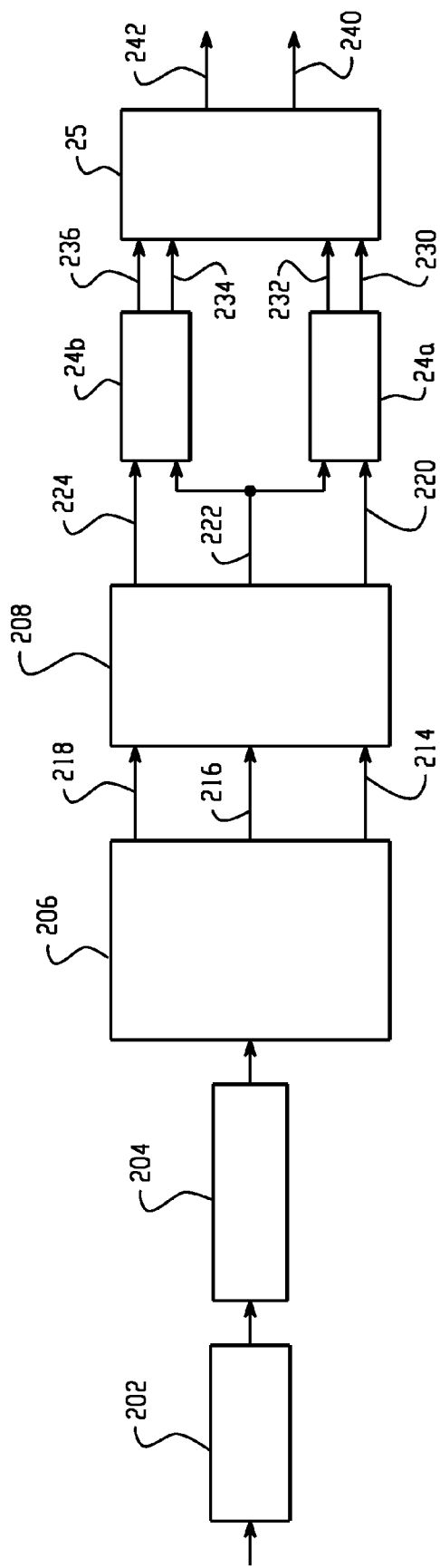
FIG. 2 is a block diagram of a portion of a data acquisition system together with an integrator and a combiner.

Turning now to FIG. 2, the data acquisition system 23 includes a signal conditioner 202, a differentiator 204, a discriminator 206, and an integrator 208 associated with each detector element 100. Also depicted are the first 24a and second 24b correctors and the combiner 25. Though not explicitly shown, those skilled in the art will appreciate that one or more multiplexers are disposed between the integrators 208 and the correctors 24.

The signal conditioner 202 amplifies and filters the signals generated by its associated detector element 100. The filter characteristics are preferably selected to filter relatively high frequency electrical and other noise while passing relatively lower frequency components associated with the rise and fall of the signals generated by the detector element 100 in response to x-ray photons. Depending on the characteristics of the detector elements 100 and the downstream processing circuitry, other or different signal conditioning functionality may be provided, or some or all of the signal conditioning functionality may be omitted.

The differentiator 204 provides an output indicative of the rate of change of the signals produced by the detector element 100 in response to the detected x-radiation. Increasing signals (i.e., those produced in response to a detected photon) result in a differentiator output signal having a first polarity, whereas decreasing signals (i.e., resulting from the decay of the detector element 100 output following detection of a photon) will produce an output signal having a second polarity. The amplitude of the differentiator 204 output is a function of the rate of change of the signal produced by the detector element 100 and thus indicative of the energy of the detected photons.

Figure 3:
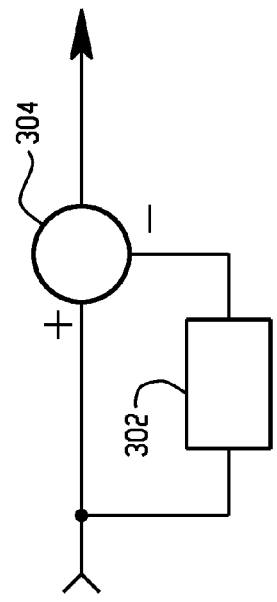
FIG. 3 depicts an implementation of a differentiator.

The differentiator 204 may be implemented using conventional differentiator circuitry such as an operational amplifier based differentiating circuit. With reference to FIG. 3, another exemplary implementation includes a delay 302 and a subtractor 304. The delay 302 provides a delay approximately equal to the detector signal total rise time, for example on the order of about 3-10 nanoseconds (ns) in the case of the aforementioned fast detectors.

A discriminator 206 classifies the detected photons into to or more energy ranges or windows. While FIG. 2 depicts a three level discriminator 206, the number of levels is selected based on the desired dynamic range and energy discrimination of the device. For example, the discriminator 206 may be implemented as a two level discriminator, particularly in systems where relatively higher count rates are not anticipated. Four or more levels may also be implemented.

In the case of a three level discriminator, the discriminator 206 produces first 214, second 216, and third 218 output signals as follows:

| Input Signal | First Output Signal 214 | Second Output Signal 216 | Third Output Signal 218 |
|---|---|---|---|
| Signal > Threshold 3 | False | False | True |
| Threshold 3 > Signal > Threshold 2 | False | True | False |
| Threshold 2 > Signal > Threshold 1 | True | False | False |

Thus, the first output signal is triggered if the signal provided by the differentiator 204 is greater than a first threshold and less than a second threshold. Illustratively, one can describe the purpose of the different thresholds as follows. The first threshold is preferably selected to block noise while passing signals indicative of radiation detected by the detector element 100. The second threshold is selected to differentiate between first and second photon energy ranges or windows. The third threshold is selected to account for relatively high count rates and pile-ups. In practice these pile-ups can introduce deviations in each of the threshold ranges, and can be corrected as described below.

In an exemplary implementation, the discriminator 206 includes one or more comparators. The various thresholds can be fixed for a particular scanner. They may also be adjustable based on the requirements of a particular scan, for example where it is desirable to distinguish between different energy ranges.

The discriminator outputs 214, 216, 218 trigger the integrator 208, which produces first 220, second 222, and third 224 outputs indicative of the number and energy of the detected x-ray photons. The counting or integration is preferably performed during the duration of a reading and reset prior to commencing a new reading.

In one implementation, the integrator 208 integrates or counts the number of output pulses produced by the various outputs of the discriminator 206. With reference to FIG. 4a, the integrator 208 includes a plurality of counters 402, 404, 406, the number of which preferably corresponds to the number of levels detected by the discriminator 206. Each counter 402, 404, 406 is incremented when corresponding output signal 214, 216, 218 from the discriminator 206 transitions to true.

In another implementation, the integrator 208 provides an indication of the total time during which the various output signals produced by the discriminator 206 are true. With reference to FIG. 4b, the integrator 208 contains a plurality of integrators 420, 422, 424, the number of which preferably corresponds to the number of levels detected by the discriminator 206. A reference 426 such as a voltage or current source provides a reference signal to each integrator 420, 422, 424. Each integrator 420, 422, 424 integrates the reference value during the time period in which the corresponding discriminator output signal 214, 216, 218 is true. The integrators 420, 422, 444 may also be implemented by counters which are clocked during the time period in which the corresponding discriminator output signal 214, 216, 218 is true.

In another implementation, the integrator 208 integrates the value of the output of the differentiator 204 during the time periods in which the respective discriminator 206 output signals are true. With reference to FIG. 4c, each integrator 420, 422, 424 receives the respective output of the differentiator and integrates this value during the time period in which the corresponding discriminator output signal 214, 216, 218 is true.

Returning to FIG. 2, the first corrector 24a corrects the first 220 and second 222 outputs produced by the integrator to produce corrected outputs 230, 232 indicative of the photons detected at the first and second energy ranges. In relatively low x-ray count rate situations where the probability of pile-ups is relatively low, individual photons or events can be detected relatively accurately and the measured values 220, 222 are approximately a linear function of the true photon numbers. As the count rate increases, however, the linearity of the measurement tends to decrease. For example, the likelihood of pile-ups increases with an increase in count rate, so that two or more events may be treated as a single event or count. Moreover, the discriminator 206 may classify overlapped events in a higher energy window. As the relationship between the true photon numbers and the measured values is relatively predictable (up to statistical errors), the effect of these deviations may be reduced. When the count rate is higher, the accuracy of the correction is on one hand deteriorated due to the additional pile-ups but on the other hand it tends to improve due to the smaller statistical error in the photon numbers. Accordingly, the correction remains relatively accurate over a range of count rates, especially for CT and other applications where the energy resolution requirements are relatively less stringent.

The first corrector 24a provides first and second corrected output values 230, 232 according to the relations:

$N1 = f1(L1,L2)$ $N2 = f2(L1,L2)$      Equation 1 where $N_x$ is the corrected count value at energy window x, $f_x$ is the correction function at energy window x, L1 is the first output 220 of the integrator, and L2 is the second output 222 of the integrator.

A second corrector 24b used at relatively higher count rates corrects the second 222 and third 224 integrator outputs to produce additional first and second corrected outputs 234, 236 indicative of the photons detected at the first and second energy ranges. As the count rate continues to increase, a significant portion of the signals produced by the detector elements 100 tend to overlap more completely, and the output of the differentiator 204 will have a relatively higher average value. The first output 214 of the discriminator will be relatively lower than the true reading, while the third output 218 of the discriminator 206 will be relatively higher. As the relationship between the true photon numbers and the measured values is relatively predictable (up to statistical errors), the effect of this deviation may be reduced.

The second corrector 24b provides corrected output values 234, 236 according to the relations:

$P1 = g1(L2,L3)$ $P2 = g2(L2,L3)$      Equation 2 where $P_x$ is the corrected count value at energy window x, $g_x$ is the correction function at energy window x, L2 is the third output 222 of the integrator, and L3 is the third output 224 of the integrator.

Overall, the first corrector 24a provides correction for a first relatively lower range of count rates, while the second corrector 24b provides corrections at higher count rates.

An optional combiner 25 combines the outputs of the first 24a and second 24b correctors as a function of the count rate to produce outputs 240, 242 indicative of the photons detected at the first and second energy ranges. In one implementation, the first outputs 230, 234 of the first and second correctors are weighted as a function of the photon count rate to generate the first output 240, while the second outputs 232, 236 of the first and second correctors are weighted as a function of the photon count rate to generate the second output 242. For example, at relatively low count rates, the outputs 230, 232 may be used exclusively to produce the first and second outputs 240, while at relatively high count rates, the outputs 234, 236 may be used exclusively. At intermediate count rates, the outputs of the first 24a and second 24b correctors are combined using a linear or other suitable weighting function. Other suitable combination functions may also be implemented.

As noted above, the third level of the discriminator 206, the third integrator 406, the second corrector 24b, and the combiner 25 may be omitted depending on the characteristics of the detector elements 100 and the anticipated count rates.

The correction functions $f_x$ and $g_x$ can be established by way of a simulation or by scanning one or more phantoms having differing, known radiation attenuation and material compositions at various count rates.

Determination of the correction functions $f_x$ and $g_x$ according to a simulation will now be described. The response of a detector element 100 can be modeled by the equation:

$$\text{DetectorOutput} = Ae^{(-t/T_d)}(1-e^{(-t/T_r)}) \quad \text{Equation 3}$$

where A is an amplitude related to photon energy, $T_d$ is the detector decay time constant, and $T_r$ is the detector rise time constant.

FIG. 5 depicts a series of pulses generated as a response 502 to simulated x-ray photons at an exemplary mean count rate of 20 million counts/sec. In the example of FIG. 5, $T_d$ is set at 30 ns, $T_r$ is set at 4 ns, and the time response or dead time of the data acquisition system 26 is set to 9 ns. Incoming photons were simulated as having random energies consistent with the spectrum of a typical x-ray tube, and the temporal distribution of the incoming photons follows Poisson statistics at the mean count rate. The above simulation parameters are exemplary and the use of other parameters is contemplated based on the characteristics of a particular detector and data acquisition system.

As can be seen in FIG. 5, many of the events overlap as a result of pulse pile-up. In order to more clearly show the overlapping effect, the simulation was conducted without noise. In an actual simulation, however, it is desirable to also consider the effects of detector signal noise, especially noise originating from the Poisson statistics of optical photons generated by the detector scintillator (or electron-hole number in the case of a direct conversion detector).

As will be appreciated, the overlapping depicted in FIG. 5 makes it difficult to determine the energy of the detected photons by integrating the area under the curve. FIG. 6 depicts the simulated output signal 602 produced by the differentiator 204, where the differentiator includes a delay 302 of 10 ns and a subtractor 304 as depicted in FIG. 3. Rising signals indicative of detected signals appear as positive signals, while the respective decay fragments appear as negative signals. The amplitude of the positive signals provides an estimate of the energy of the detected x-ray photons.

To determine the correction functions, the actual photon numbers generated by the simulation during a reading time period in each of the energy windows for a given input photon count rate are determined. The corresponding output values 220, 222, 224 produced by the integrator 208 are also determined. This process is repeated for a desired number of different count rates and energy spectra.

After passing through the scanned object, the energy distribution of the detected photons is affected by the material composition of the object. With reference to FIG. 7, spectrum 702 simulates a first relatively softer or lower energy spectrum resulting from passing though an object with a relatively low radiation attenuation response. Spectrum 704 simulates a relatively harder spectrum resulting from passing through an object with higher radiation attenuation response. Spectrum 706 depicts a composite spectrum which is the average of the first 702 and second 704 spectra and is used in a subsequent simulation step. The vertical axis represents the normalized intensity as a function of energy; the total number of photons may be substantially different. The two peaks in the spectra 702, 704, 706 are simulations of the peaks in the output of a typical tungsten anode x-ray tube.

Results of an exemplary simulation using an integrator 208 as described in FIG. 4a are depicted in FIG. 8. The actual photon count rates as a function of the input count rate in the first and second energy windows for the first energy spectrum 702 are depicted at 802 and 804, respectively. The actual count rates in the first and second energy windows for the second energy spectrum 704 are likewise depicted at 806 and 808 respectively. As the curves 802, 804, 806, 808 represent the actual count rates, it will be appreciated that each curve is a straight line. The measured photon count rates as determined using the first 220 and second 222 outputs of the integrator 208 in the first and second energy windows for the first energy spectrum 702 are depicted at 810 and 812, respectively. The measured photon count rates in the first and second energy windows for the second energy spectrum 704 are depicted at 814 and 816, respectively. As can be seen, the slope of the measured count rates 810, 812, 814, 816 begins to decrease as the count rate increases.

The relationships between the corresponding measured and actual count rates are used to calculate the correction functions f1 and f2. Note that, for the purposes of the simulation, separate intermediate correction functions f1 and f2 are generated for each energy spectrum 702, 704.

As will also be appreciated, the correction functions f1 and f2 provide unique results over count rates in which the slope of the measured curves 810, 812, 814, 816 remains positive, which in the exemplary simulation is true for count rates up to about $4 \times 10^7$ counts per second. Above this rate, the high count rate correction functions g1 and g2 are advantageously used.

Final correction functions f1 and f2 are obtained by performing a bilinear interpolation of the corresponding results from the first 702 and second 704 spectra in order to cover an intermediate spectrum 706, which in the example of FIG. 7 is the average of the first 702 and second 704 spectra. The final correction functions f1, f2 may advantageously be implemented as first and second lookup tables. The structure of each lookup table includes two independent variables and one dependent variable, where the independent variables are the first 220 and second 222 outputs of the integrator and the dependent variable is the corrected count value for the relevant energy window (e.g., N1 for the first lookup table, and N2 for the second look-up table). Alternately the final correction functions f1, f2 may be implemented as a single lookup table, where the respective output values N1, N2 are accessed as a function of the first 220 and second 222 integrator outputs. Of course, the correction functions may be implemented using other suitable methods, for example via direct mathematical calculations. It should also be noted that the corrections may be performed as part of the reconstruction of the data from the scan.

The accuracy of the correction can be estimated by performing a further simulation using the third energy spectrum 706 and the previously calculated correction functions. The actual outputs of a series of simulations are then compared against the actual input values.

A similar simulation is performed at the relatively higher count rates to determine the correction functions g1 and g2.

The energy resolution of the described techniques may be much lower than the energy resolution that can be obtained by integrating the whole pulse. Nonetheless, it allows for discriminating between two energy ranges, with some mutual overlapping.

In operation, an object under examination is scanned. As the detector 20 rotates about the examination region, each detector element 100 produces an output signal indicative of detected x-ray photons. Following any required signal conditioning, the differentiator 204 produces an output signal indicative of the rate of change of the detector element 100 signal. The discriminator 206 classifies the detected events into one or more energy levels or windows. The output of the discriminator 206 triggers an integrator 208, which produces outputs indicative of the x-ray photons detected at each energy window. Similar outputs are generated for each detector element 100 and for each of a plurality of reading periods.

For signals obtained at relatively low count rates, the first corrector 24*a* uses the first 220 and second 222 outputs of the discriminator 206 to produce corrected outputs indicative of the number and energy distribution of the detected photons. At relatively higher count rates, a second corrector 24*b* uses the second 222 and third 224 discriminator outputs to generate corrected outputs. A combiner 25 may be used to combine the outputs of the first 24*a* and second 24*b* correctors to produce a final output values indicative of the number and energy distribution of the detected x-ray photons. The information is further processed by the reconstructor 22 and made available to the operator via the console 44.

Of course, modifications and alterations will occur to others upon reading and understanding the preceding description. It is intended that the invention be construed as including all such modifications and alterations insofar as they come within the scope of the appended claims or the equivalents thereof.

The invention claimed is:

1. An apparatus comprising:
   a radiation sensitive detector which produces an output in response to ionizing radiation;
   a discriminator which produces first and second outputs based on the rate of change of the detector output;
   a first integrator triggered by the first discriminator output and which generates a first integrator output;
   a second integrator triggered by the second discriminator output and which generates a second integrator output;
   a first corrector which uses the first and second integrator outputs to generate a first output indicative of detected radiation having a first energy range and a second output indicative of detected radiation having a second energy range, wherein the first corrector corrects for pulse pile-ups in the detector output.

2. The apparatus of claim 1 wherein the discriminator produces a third output indicative of the rate of change of the detector output, wherein the apparatus further comprises a third integrator triggered by the third discriminator output and which generates a third integrator output, and wherein the apparatus further comprises a second corrector which uses the second and third integrator outputs to generate a first output indicative of detected radiation having the first energy range and a second output indicative of detected radiation having the second energy range.

3. The apparatus of claim 2 wherein the first corrector corrects for pulse pile-ups at a first range of radiation photon count rates and the second corrector corrects for pulse pile ups at a second range of radiation photon count rates which is higher than the first range of radiation photon count rates.

4. The apparatus of claim 3 further including means for weighting the first output of the first corrector and the first output of the second corrector as a function of the radiation photon count rate to generate a first weighted output and for weighting the second output of the first corrector and the second output of the second corrector as a function of the radiation photon count rate to generate a second weighted output.

5. The apparatus of claim 1 wherein the first integrator counts the number of times the first integrator is triggered by the first discriminator output.

6. The apparatus of claim 1 wherein the first integrator generates an output indicative of the length of time during which the first integrator is triggered by the first discriminator output.

7. The apparatus of claim 1 wherein the first integrator integrates a value indicative of the rate of change of the detector output when triggered by the first discriminator output.

8. The apparatus of claim 1 including a differentiator which subtracts a time shifted detector output from the detector output to generate a signal indicative of the rate of change of the detector output.

9. The apparatus of claim 1 including an x-ray tube which rotates about an examination region and wherein the detector generates an output indicative of x-radiation emitted by the x-ray source which has traversed the examination region.

10. A method comprising:
    measuring a rate of change of an output signal produced by a radiation sensitive detector in response to an ionizing radiation photon;
    updating a first value if the rate of change is in a first range;
    updating a second value if the rate of change is in a second range;
    repeating the steps of measuring, updating the first value, and updating the second value for a plurality of photons;
    generating a first output indicative of photons detected in a first energy range, wherein the first output is a function of the first and second values;
    generating a second output indicative of photons detected in a second energy range, wherein the second output is a function of the first and second values.

11. The method of claim 10 wherein the step of generating includes correcting for pulse pile-ups in the detector output.

12. The method of claim 10 wherein the step of updating a first value includes counting the number of times the rate of change of the detector output is in the first range.

13. The method of claim 10 wherein the step of updating the first value includes updating the first value as a function of the time period during which the rate of change of the detector output is in the first range.

14. The method of claim 10 wherein the step of repeating includes repeating for a reading time period.

15. The method of claim 10 wherein the step of generating a first output includes using the first and second values to access a lookup table.

16. The method of claim 10 further including updating a third value if the rate of change of the detector output is in a third range.

17. The method of claim 16 wherein the first output is a function of the second and third values, and the second output is a function of the second and third values.

18. A method comprising:
    estimating the energy of an ionizing radiation photon detected by a radiation sensitive detector;
    updating one of at least first and second values depending on the estimated energy;
    repeating the steps of estimating and updating for photons detected during a pre-selected time period;
    using the first and second values to generate a first output indicative of detected photons having a first range of energies and a second output indicative of detected photons having a second range of energies, wherein the first and second outputs include corrections for detector pulse pile ups.

19. The method of claim 18 wherein the step of updating includes updating one of at least first, second, and third values depending on the estimated energy and wherein the step of using includes using, depending on a photon count rate, at least one of (i) the first and second values and (ii) the second and third values to generate the first output and at least one of (i) the first and second values and (ii) the second and third values to generate the second output.

20. The method of claim 18 wherein the step of updating includes updating a count.

* * * * *